United States Patent [19]

Schwarz

[11] Patent Number: 4,694,290
[45] Date of Patent: Sep. 15, 1987

[54] READINESS INDICATOR FOR LASER MEDICAL INSTRUMENTS

[75] Inventor: Jürgen Schwarz, Oberkochen, Fed. Rep. of Germany

[73] Assignee: Carl-Zeiss-Stiftung, Heidenheim on the Brenz, Fed. Rep. of Germany

[21] Appl. No.: 699,022

[22] Filed: Feb. 7, 1985

[30] Foreign Application Priority Data

Feb. 15, 1984 [DE] Fed. Rep. of Germany ....... 3405308

[51] Int. Cl.$^4$ ............................................. G08B 21/00
[52] U.S. Cl. ........................... 340/815.21; 128/303.1; 340/407; 340/540; 340/600
[58] Field of Search .................. 340/815.21, 540, 600, 340/635, 825.19, 407; 128/303.1

[56] References Cited

U.S. PATENT DOCUMENTS 3,925,770 12/1975 Beacham et al. .............. 340/600
4,478,217 10/1984 Shimada et al. ............... 128/303.1
4,556,875 12/1985 Ishiwatari ..................... 128/303.1

*Primary Examiner*—Glen R. Swann, III
*Attorney, Agent, or Firm*—Stonebraker, Shepard & Stephens

[57] ABSTRACT

Readiness for operation of laser medical instruments or of flash generators for ophthalmological instruments is indicated in such a way that the readiness signal is perceptible only to the physician and not to the patient being operated upon. There is a mini-earphone to be worn in an ear of the physician. The conventional readiness signal, if of the optical kind, is converted to an audible signal delivered to the earphone of the physician. A photodiode responsive to the optical signal is part of the conversion system, which also includes an audiogenerator and an amplifier. If the conventional readiness signal is of the audible kind, the loudspeaker is rendered inoperative and a sound signal is produced in the earphone. In addition to the advantage that the readiness signal is perceptible only to the physician and not to the patient, a further advantage is that the physician does not have to turn his head or shift his gaze from the desired concentration on viewing the operating area, in order to see a signal light, as is necessary in prior art signals of the optical variety.

6 Claims, 2 Drawing Figures

READINESS INDICATOR FOR LASER MEDICAL INSTRUMENTS

BACKGROUND OF THE INVENTION

This invention relates to a device for indicating the readiness or operation of laser medical instruments, such as instruments used in ophthalmology, which is an important field of use of laser instruments.

For example, when treating a cataract in the eye, protein fibrils which cause a clouding of the lens or vitreous body of the eye are to be destroyed. For this purpose, it is preferable to use lasers which emit a chain of pulses when a given pump light energy is reached, the chain of pulses consisting of a plurality of individual pulses which, when focused, produce a spontaneous ionization of matter.

Patients have reported that the high laser outputs, they feel a pressure in the eye when the laser pulses impinge thereon, but the pressure is not considered painful. In order to prevent the patient from establishing a relationship between the indication of readiness for operation of the laser and the perception of pressure in the eye, and possibly reacting thereto, it is desirable that the signal or indication of readiness for operation of the laser be not perceptible to the patient, but only to the doctor. The present invention accomplishes this.

Indicating devices are known in the art, which indicate that the treatment laser is ready or operation by giving an optical signal i.e., a visible indication such as a pilot light. One such device is disclosed, for instance, in German Federal Republic Offenlegungsschrift (unexamined patent application) No. 28 32 847, of J. Eichler et al., published Feb. 14, 1980, International Class A61B 17/36. This device has the disadvantage that the treating physician must shift his glance from the operating field to the indicating device in order to be informed when the laser is ready for operation, and this disturbs his concentration on the operating field.

SUMMARY OF THE INVENTION

The object of the present invention is to provide an indicating device which is perceptible only to the physician and not to the patient, and which does not in any way divert his attention from the operating field.

This object is achieved by coupling an existing indicating device to an audiogenerator with amplifier, and conducting the sound signal produced thereby to an earphone worn in the ear of the physician, so that the sound signal is apparent only to the physician and is not heard by the patient. In this way the physician is apprised aurally of the readiness of the laser for operation, without removing his gaze from the operating area which he is examining, e.g., through an operation microscope.

In one embodiment of the invention, an audiogenerator plus amplifier is operatively connected via a photodiode to an existing optical indicating device, and the physician's earphone is connected to the output of the amplifier. The photodiode is responsive to the light signal emitted by the indicating device.

In another embodiment of the invention, where the existing indicating device gives an acoustic signal rather than an optical signal, the connecting line going to the loudspeaker or beeper of the existing device is interrupted by a switching jack, and the audiogenerator plus amplifier is plugged into the switching jack, rendering the existing loudspeaker or beeper inoperative and sending the signal through the audiogenerator-amplifier to the miniature earphone in the physician's ear.

An advantage of the present invention is the ease with which it may be reduced to practice; that is, the ease with which an existing conventional readiness indicator, whether of the optical type or of the audible type, may be quickly and easily converted so that the signal is received only by the physician, audibly in his ear alone, without giving any indication to the patient, and without requiring the physician to turn his head or shift his glance toward a visual indicator, and without distracting his attention from full concentration on the observation of the operating field or area.

DESCRIPTION OF THE PREFERRED EMBODIMENTS

Figure 1:
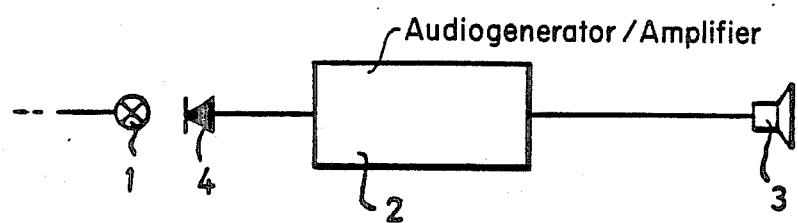
FIG. 1 is a schematic illustration of one embodiment of the invention, as applied to an existing conventional optical indicating device.

Referring first to FIG. 1, the numeral 1 indicates schematically the optical output of any existing conventional readiness indicator of the optical signal type, e.g., a pilot light which comes on (is illuminated) when an associated ophthalmic operation laser is ready to operate. The rectangle 2 indicates an audiogenerator and associated amplifier, which may be of any conventional known construction, the details of which are unimportant for purposes of the present invention. The audio output of the amplifier passes through a conductor cord to the mini-earphone 3, of any conventional known construction.

A photodiode 4 of conventional construction is operatively connected to the input of the audiogenerator-amplifier unit 2, and is positioned to receive light from the optical indicator 1 of the conventional readiness indicator. When the readiness indicator gives the signal that the laser (or other instrument) is ready for operation, the light from the lamp 1 activates the photodiode 4, and the unit 2 sends an audible signal to the earphone 3 in the ear of the physician.

Figure 2:
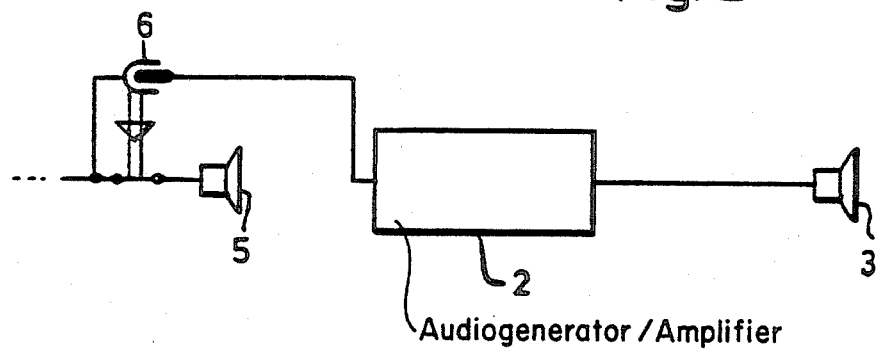
FIG. 2 is a schematic illustration of another embodiment of the invention, as applied to an existing conventional acoustical indicating device.

In the embodiment illustrated in FIG. 2, the conventional readiness indicator shown schematically at the left of the view is of the audible signal type rather than the optical signal type which was shown in FIG. 1. Normally it produces an audible signal through the loudspeaker 5. But this would be desirable under the ophthalmic operation circumstances mentioned above, because it would be heard by the patient being operated upon, as well as by the physician. Therefore, according to the invention, the circuit leading to the speaker 5 is provided with a switching jack 6 of the known type in which, when a plug is inserted into the jack, the signal circuit to the speaker 5 is broken and the signal energy goes to the plug. From the plug, a circuit leads to the unit 2, as illustrated.

This embodiment operates similarly to the first embodiment. When the conventional readiness indicator indicates that the laser or other instrument is ready for operation, no sound issues from the speaker 5 but instead, the signal energy goes from the jack 6 to the inserted plug, thence to the unit 2, and an audible signal is produced in the mini-earphone 3 in the ear of the physician.

What is claimed is:

1. A device for indicating the readiness for operation of a laser medical instrument, said device comprising an audiogenerator and amplifier unit having an input and an output, an earphone operatively connected to said output, and an operative connection from an existing indicating device to said input of said unit, whereby a signal given by said existing indicating device will cause a signal to be delivered to said earphone.

2. The invention defined in claim 1, wherein said existing indicating device is an optical indicating device, and said operative connection from said existing device to said unit includes a photodiode responsive to a light signal from said existing device.

3. The invention defined in claim 1, wherein said existing indicating device is an acoustical indicating device having a loudspeaker, and said operative connection to said input includes a switching jack which renders said loudspeaker inoperative when said operative connection is established to said input of said unit.

4. A device for indicating operative readiness of a medical instrument in such a way that a readiness signal is preceptible only to a physician operating the instrument and not perceptible to a patient being operated upon, said device comprising a source signal for indicating readiness, an intermediate unit having an input and an output, an earphone to be worn in an ear of said physician, transmission means operatively connecting said earphone to said output of said unit, and means responsive to said source signal for causing said intermediate unit to deliver a signal through said transmission means to said earphone.

5. The invention defined in claim 4, wherein:
(a) said source signal is an inaudible optical signal;
(b) said means responsive to said source signal includes a photodiode positioned to receive light from said optical signal; and
(c) said intermediate unit includes an audiogenerator and an amplifier.

6. The invention defined in claim 4, wherein:
(a) said source signal is an audiofrequency signal normally connected to a loudspeaker; and
(b) said means responsive to said source signal includes means for transmitting said audiofrequency signal to said input of said intermediate unit and operatively disconnecting said audiofrequency signal from said loudspeaker.

* * * * *

UNITED STATES PATENT AND TRADEMARK OFFICE
CERTIFICATE OF CORRECTION

PATENT NO. : 4,694,290
DATED : Sep. 15, 1987
INVENTOR(S) : Jurgen Schwarz

It is certified that error appears in the above-identified patent and that said Letters Patent is hereby corrected as shown below:

Column 1, line 7, delete "or" and substitute --for--.

Column 1, line 18, delete "the" and substitute --with--.

Signed and Sealed this

Twenty-sixth Day of January, 1988

Attest:

DONALD J. QUIGG

*Attesting Officer*  *Commissioner of Patents and Trademarks*